United States Patent [19]
Renauld et al.

[11] Patent Number: 5,962,269
[45] Date of Patent: Oct. 5, 1999

[54] METHODS FOR PRODUCING ANTIBODIES WHICH SPECIFICALLY BIND TO INTERLEUKIN-9 RECEPTOR

[75] Inventors: Jean-Christophe Renauld, Herbeunont; Catherine Druez, Sint-Stevens-Woluwe; Jacques Van Snick, Kraainem, all of Belgium

[73] Assignee: Ludwig Institute for Cancer Research, New York, N.Y.

[21] Appl. No.: 08/456,489

[22] Filed: Jun. 1, 1995

Related U.S. Application Data

[62] Division of application No. 08/164,614, Dec. 8, 1993, Pat. No. 5,789,237, which is a continuation of application No. 07/847,347, Mar. 9, 1992, abandoned.

[51] Int. Cl.⁶ .............................. C12P 21/04; C12P 21/08; C12N 5/00; C07K 16/00
[52] U.S. Cl. .................... 435/69.6; 435/70.21; 435/71.1; 435/326; 435/331; 435/334; 530/387.1; 530/387.9; 530/388.22
[58] Field of Search .............................. 530/387.1, 387.9, 530/388.22; 435/69.6, 70.21, 71.1, 326, 331, 334

[56] References Cited

U.S. PATENT DOCUMENTS 4,965,195  10/1990  Namen et al. .
5,246,701   9/1993  Dugas et al. .

OTHER PUBLICATIONS

Sevier et al Clinical Chemistry vol. 27 No. 11 pp. 1797–1806, 1981.

Lazar et al (Molecular & Cellular Biology vol. 8, No. 3, Mar. 1988 pp. 1247–1252).

Burgess et al (J. of Cell Biolgy vol. 111, Nov. 1990 pp. 2129–2138).

Salgaller et al (Cancer Immunol. Immunother. vol 39, 1994 pp. 105–116).

*Primary Examiner*—Anthony C. Caputa
*Assistant Examiner*—Mark Navarro
*Attorney, Agent, or Firm*—Fulbright & Jaworski, LLP

[57] ABSTRACT

The invention describes nucleic acid sequences which code for the interleukin 9 receptor (IL9-R) molecule. These sequences may be used as probes to identify cells expressing the molecule, and as agents to transfect recipient cells.

9 Claims, 3 Drawing Sheets

FIG. 2

```
m   MALGRCIAEGWTLERVAVKQV--SWFLIYSWVCSGVCRGVSVPEQGGGGQKAGAFTCLSNSIYRIDCHWSAPELGQESRAWLLFTSNQVTEIKHKCTF    96
    | |||| ||||||   |     |  ||| || | | || |||| ||||||  ||||| |||||||||||||||||||||
h   MGLGRCIWEGWTLESEALRRDMGTWLLACICICTCVCLGVSVTGEGQGPR-SRTFTCLTNNILRIDCHWSAPELGQGSSPWLLFTSNQAPGGTHKCIL    97 m   WDSMCTLVLPKEEVFLPFDNFTITLHRCIMGQEQVSLVDSQYLPRRHIKLDPPSDLQSNVSSGRCVLTWGINLALEPLITSLSYELAFKRQEEAWE-A   193
    ||| | ||| ||| || ||| |||  ||   |||||| |||||||| ||||||| ||| ||||| | ||||  || ||| ||||||| ||||| | |
h   RGSECTVVLPPEAVLVPSDNFTITFHHCMSGREQVSLVDPEYLPRRHVKLDPPSDLQSNISSGHCILTWSISPALEPMTLLSYELAFKKQEEAWEQA   195 m   RHKDRIVGVTWLILEAVELNPGSIYEARLRVQM-TLESYEDKTEGEYYKSHWSEWSQPVSFPSPQRRQGLLVPRWQMSASILVVVPIFLLLTGFVHLL   290
    | ||||||||||| |||| ||| ||||||||| | ||| ||  ||   |||||| |||| || |||  |||| |||    ||||  ||||||| ||
h   QHRDHIVGVTWLILEAFELDPGFIHEARLRVQMATLEDDVV--EEERYTGWSEWSQPVCFQAPQ-RQGPLIPPWGWPGNTLVAVSIFLLLTGPTYLL   290 m   FKLSPRLKRIFYQNIPSPEAFFHPLYSVVHGDFQSWTGARRAGPQARQNGVSTSSAGSESSIWEAVATLTYSPACPVQFACLKWEATAPGFPGLPG--   386
    |||||| |||||||  ||| || |||||  ||    |||    |||    ||| || || ||| |   |   |  |  |   | ||  ||| |
h   FKLSPRVKRIFYQNVPSPAMFFQPLYSVHNGNFQTWMGAHRAGVLLSQDCAGTPQGALEPCVQEATALLTCGPARPWKSVALEEEQEGPGTRLPGNLS   388 m   SEHVLPAGCLELEGQPSAYLPQEDWAPLGSARPPPPDS------DYCMLDCCEECHLSAFPGHTESPELTLAQPVALPVSSRA                  468
    ||||||||| ||||  | ||||||||  |  |  |  |             ||      |                |
h   SEDVLPAGCTEWRVQTLAYLPQEDWAPTSLTRPAPPDSEGSRSSSSSSSNNNNYCALGCYGGWHLSALPGNTQSSGPIPALACGLSCDHQGLETQQ      486 h   GVAWVLAGHCQRPGLHEDLQGMLLPSVLSKARSWTF                                                                 522
```

METHODS FOR PRODUCING ANTIBODIES WHICH SPECIFICALLY BIND TO INTERLEUKIN-9 RECEPTOR

RELATED APPLICATIONS

This application is a Divisional of Ser. No. 08/164,614 filed Dec. 8, 1993, now U.S. Pat. No. 5,789,237, which in turn is a continuation of Ser. No. 07/847,347 filed Mar. 9, 1992, abandoned.

FIELD OF THE INVENTION

This invention relates to the reception of the cytokine known as interleukin 9 by cells, via its receptor. More particularly, it relates to the isolation of nucleic acid sequences which code for interleukin 9 receptor molecules ("IL-9R" hereafter). These sequences can be used, e.g. as a source for IL-9 receptor, and as probes for cells which respond to the cytokine. The complementary sequences can be used to inhibit expression as well as to probe for the coding sequences.

BACKGROUND AND PRIOR ART

The last decade has seen knowledge of the immune system and its regulation expand tremendously. One area of particular interest has been that of research on the proteins and glycoproteins which regulate the immune system. Perhaps the best known of these molecules, which are generically referred to as "growth factors", "cytokines", "leukotrines", "lymphokines", etc., is interleukin-2 ("IL-2"). See, e.g., U.S. Pat. No. 4,778,879 to Mertelsmann et al.; U.S. Pat. No. 4,490,289, to Stern; U.S. Pat. No. 4,518,584, to Mark et al.; and U.S. Pat. No. 4,851,512 to Miyaji et al. Additional patents have issued which relate to interleukin 1—("IL-1"), such as U.S. Pat. No. 4,808,611, to Cosman. The disclosure of all of these patents are incorporated by reference herein.

In order for molecules such as IL-2 and IL-1 to exert their effect on cells, it is now pretty much accepted that these must interact with molecules, located on cell membranes, referred to as receptors. Patents which exemplify disclosures of interleukin receptors include Honjo et al., U.S. Pat. No. 4,816,565; and Urdal et al., U.S. Pat. No. 4,578,335, the disclosures of which are incorporated by reference. Recently, Fanslow, et al., Science 248: 739–41 (May 11, 1990) presented data showing that the effect of IL-1 in vivo could be regulated via the administration of a soluble form of its receptor. The last paragraph of the Fanslow paper, the disclosure of which is incorporated by reference, describes the types of therapeutic efficacy administration of soluble IL-1 receptor ("IL-1R") is expected to have.

The lymphokine IL-9, previously referred to as "P40", is a T-cell derived molecule which was originally identified as a factor which sustained permanent antigen independent growth of T4 cell lines. See, e.g., Uyttenhove, et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed to act on restricted T4 cell lines, failing to show activity on CTLs or freshly isolated T cells. See, e.g., Uyttenhove et al., supra, and Schmitt et al., Eur. J. Immunol. 19: 2167 (1989). This range of activity was expanded when experiments showed that IL-9 and the molecule referred to as T cell growth Factor III ("TCGF III") are identical. IL-9 enhances the proliferative effect of bone marrow derived mast cells to "IL-3", as is described by Hültner et al., Eur. J. Immunol. and in U.S. patent application Ser. No. 498,182 filed Mar. 23, 1990 the disclosures of both being incorporated by reference herein. It was also found that the human form of IL-9 stimulates proliferation of megakaryoblastic leukemia. See Yang et al., Blood 74: 1880 (1989). Recent work on IL9 has shown that it also supports erythroid colony formation (Donahue et al., Blood 75(12): 2271–2275 (Jun. 15, 1990)); promotes the proliferation of myeloid erythroid burst formation (Williams et al., Blood 76: 306–311 (Sep. 1, 1990)); and supports clonal maturation of BFU.E's of adult and fetal origin (Holbrook et al., Blood 77(10): 2129–2134 (May 15, 1991)). Expression of IL9 has also been implicated in Hodgkin's disease and large cell anaplastic lymphoma (Merz et al., Blood 78(8): 1311–1317 (Sep. 1, 1990)).

The art teaches the cloning of receptors for various members of the interleukin family. Moseley et al. Cell 59: 335–348 (1989), teach the isolation of cDNA coding for IL-4 receptors, and analysis of both genomic DNA and RNA for these molecules. To do this, Moseley et al. worked with cells exhibiting up to 1 million receptor molecules per cell, and an N-terminal amino acid sequence for IL-4 receptor. Holmes et al., Science 253: 1278–1280 (1991), and Murphy et al., Science 253: 1280–1282 (1991) discuss cDNA for the IL-8 receptor. Murphy et al. proceeded via hybridization studies, using an oligonucleotide probe based upon rabbit IL-8R amino acid sequences to isolate the human counterpart. Holmes et al. used human neutrophil CDNA libraries followed by transfection in COS cells.

Gillis, "T-cell Derived Lymphokines" in Paul, ed., Fundamental Immunology, Second Edition (New York, 1989), at pages 632 et seq. gives an overview of interleukin receptors. This reference describes cDNA for the IL1 receptor, the IL2 receptor and the IL-6 receptor.

These studies indicate that several factors are important in attempting to identify and isolate a nucleic acid sequence coding for an interleukin receptor. Ideally, one has both the amino acid sequence for the receptor and a cell type with a high degree of expression of the receptor molecule.

In the case of the interleukin 9 receptor, while Druez et al., J. Immunol. 145: 2494–2499 (1990) have identified and characterized the receptor, an amino acid sequence of the molecule is not yet available. In addition, very few cell types are known which express IL9-R (Druez, su gra), and those that do, express it at very low levels. Thus, it is surprising that it now possible to identify and to isolate nucleic acid sequences which code for the interleukin 9 receptor. This is the key feature of the invention described herein, as will be seen from the disclosure which follows.

BRIEF DESCRIPTION OF THE FIGURES

FIG. 2 aligns deduced human SEQ ID No: 1D and murine IL-9R amino acid sequences.

DETAILED DESCRIPTION OF THE PREFERRED EMBODIMENTS

EXAMPLE 1

Figure 1:
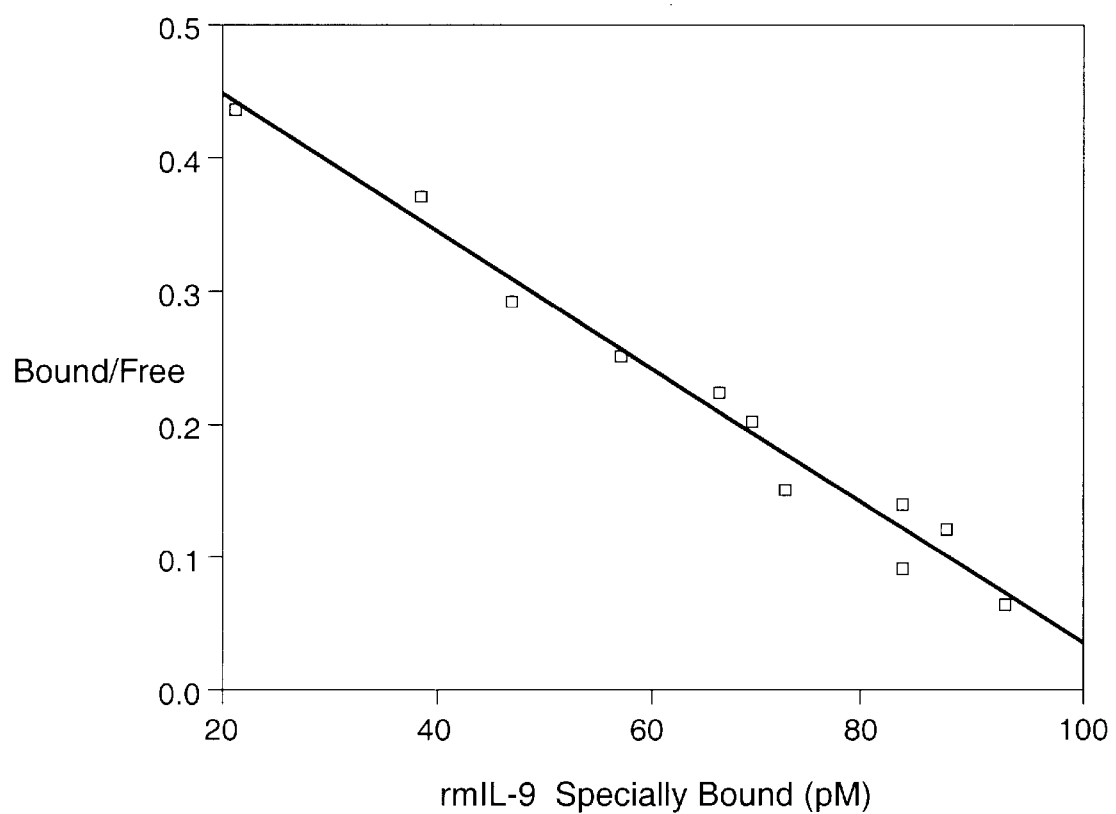
FIG. 1 presents Scatchard analysis of expression of murine IL9 receptor following transfection of COS cells.

The murine T cell clone, TS1, described by, e.g., Uyttenhove et al., Proc. Natl. Acad. Sci. 85: 6934–6938 (1988) the disclosure of which is incorporated by reference, expresses approximately 200 high affinity binding sites for IL-9, i.e., it expresses the IL-9 receptor molecule. See Druez et al., J. Immunol. 145: 2494–2499 (1990). This cell line, while presenting few receptor molecules does show the highest density of IL9R of all cells tested, and thus was selected as a source of mRNA for constructing a cDNA library.

Poly(A)+ mRNA was extracted from TS1 cells, and was then converted to double stranded cDNA using random hexanucleotide primers, following Grubler et al, Gene 25: 263–269 (1983), the disclosure of which is incorporated by reference.

Following this, EcoRI adaptors were attached, and any cDNA larger than 1.5 kilobases was isolated by fractionation on a 5–20% potassium acetate gradient, following Aruffo et al., Proc. Natl. Acad. Sci. 84: 8573–8577 (1987).

The size selected cDNA was then inserted into the ECORI site of expression vector pCDSRa taught by Takebe et al., Mol. Cell Biol. 8: 466–472 (1988). This was then transfected into E. coli strain XL1-blue using standard transformation procedures. (Maniatis). In order to screen for clones expressing IL-9R, plasmid DNA from the cDNA library was tested for the ability to express IL-9 binding activity by expression in COS cells. Basically, the cDNA library was subfractionated into 100 pools of about 500 clones each, and the DNA was transfected using the DEAE-dextran-chloroquine method of Aruffo et al., supra, into $1.5 \times 10^5$ COS cells, seeded on glass microscope slides. Cells were allowed to grow for 2–3 days, and were then tested for expression of IL-9R with $^{125}$I labelled, purified recombinant murine IL9. This labeled material was prepared following Bolton et al., Biochem. J. 133: 529–539 (1973). The cells were incubated for three hours at 20° C. with 0.2 nM of this material, washed briefly, fixed, and then dipped into liquid photographic emulsion. The slides were exposed for 10 days, then developed and examined microscopically for autoradiographic grains.

This screening resulted in two positive pools out of 100. One positive pool showed a single positive cell, and the second one showed 33 positive cells. This latter pool was selected for further testing, and was divided, first into 100 pools of 15 clones each, after which a single positive pool was selected, and divided into 100 single clones.

EXAMPLE 2

Following the separating and replating described at the end of example 1, supra, the screening methodology described therein was employed on the replated cells, and led to identification of a clone containing a plasmid referred to as p9RA1. Since the "source" plasmid pCDSRa was known and characterized, it was possible using standard methodologies to identify the insert as 1900 base pairs in length.

EXAMPLE 3

Using the p9RA1 1900 base pair segment as a probe, additional screening was carried out to identify additional murine IL9R receptor cDNA clones. The methodology followed was that of Maniatis et al., Molecular Cloning, a Laboratory Manual (Cold Spring Harbor Laboratory, New York, 1982), where the p9RA1 probe was hybridized to two further cDNA libraries which were generated in the BstXI site of vector pCDM8 (Aruffo et al, supra), using oligo T or random primers, followed by high stringency washes.

This methodology resulted in the identification of six additional clones. Two of these were oligo-dT primed cDNAs, and are referred to as p9RB1, and p9RB3, and four random primed clones p9RC2, p9RC3, p9RC4 and p9RC9. The sizes of these clones are as follows:

p9RB1 1600 bp
p9RB3 900 bp
p9RC2 2000 bp
p9RC3 1000 bp
p9RC4 3000 bp
p9RC9 2100 bp.

EXAMPLE 4

In order to make sure that clone p9RA1 and all subsequent clones did in fact express IL9R, Scatchard analysis was carried out on transfected COS cells, following Goodwin et al., Cell 60: 941–951 (1990). This analysis, shown in FIG. 1, identified a single class of binding sites with a Kd of 194 pM, when p9RA1 was used. This is slightly higher than the dissociation constant measured on TS1 cells previously, i.e., 67 pM.

When the largest cDNA was tested (i.e., the C4 clone), high affinity binding sites for IL9 were also identified, with a Kd of 126 pM.

EXAMPLE 5

Following the isolation of murine clones, tests were also carried out to isolate analogous human material. To do this, a megakaryoblast cell line, i.e., Mo7E was used as a source of mRNA to make double stranded cDNA as per example 1. The plasmid pRC/RSV was used to receive the cDNA. This cDNA library was screened, using p9RA1 as a probe, and hybridization was carried out using the same conditions described supra, except washes were carried out at low stringency (2×SSC, 0.1% SDS, 55° C.). Six clones were isolated, i.e., ph9RA2, 3, 4, 5, 6 and 9, and sequenced. The clone ph9RA3 contained a 1566 base pair open reading frame, which showed 66% identity with murine p9RC4. The deduced murine and human protein sequences are shown in FIG. 2, with a 53% identity over 522 amino acids.

EXAMPLE 6

In order to test whether clone ph9RA3 actually did code for a human IL9 receptor, the clone was transfected into murine cell line TS1, using double pulse electroporation. In brief, $5 \times 10^6$ TS1 cells were resuspended at 37° C. in 0.8 ml of Dulbecco's modified Eagle's medium, supplemented with 10% fetal bovine serum, 50 mM 2-mercaptoethanol, 0.55 mM L-arginine, 0.24 mM L-asparagine, and 1.25 mM L-glutamine. Plasmid DNA (50 μg) was added to the cells in 0.4 cm cuvettes just before electroporation. After a double electric pulse (750 V, 7452Ω, 40 μF and 100 V, 74Ω, 2100 μF), cells were immediately diluted in fresh medium supplemented with murine IL9. After 24 hours, cells were washed and cultured in the presence of G418, and mouse IL9. These conditions resulted in a frequency of transfection of approximately 1/10,000. Following selection with G418, transfected cells were maintained in human IL9, and a TS1 proliferation assay was performed using the methodology of Uyttenhove et al., Proc. Natl., Acad. Sci. USA 85: 6934–6938 (1988). If the CDNA expresses hIL9R, then cells should proliferate, while those which do not contain it should not.

Figure 3A:
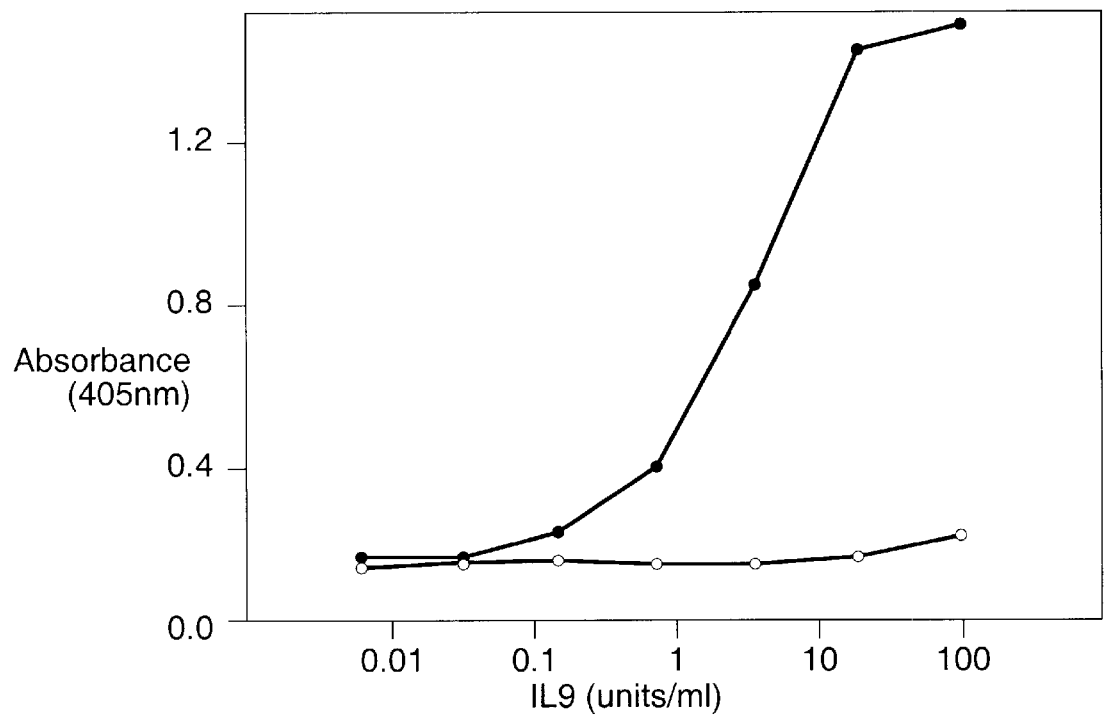
FIGS. 3A and 3B compare the response of TS1 cells, both before and after transfection with DNA coding for human IL-9R.
Figure 3B:
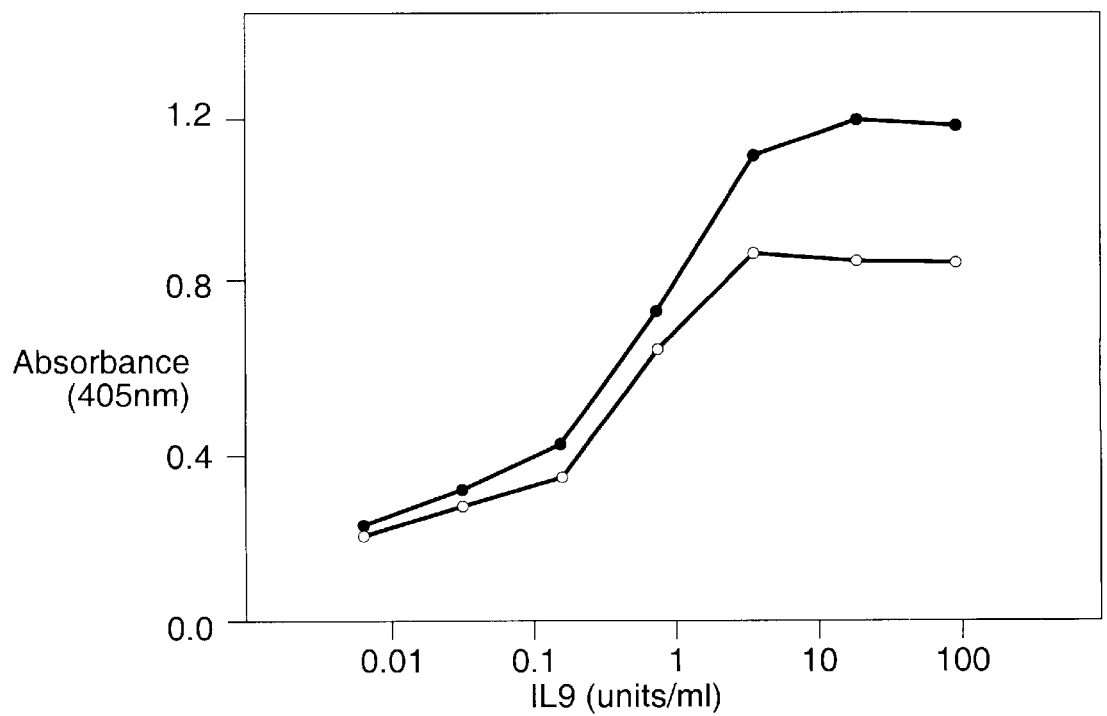

FIGS. 3A and 3B show that original TS1 cells, unresponsive to 100 units/ml of human IL9, became responsive and proliferated after transfection with the human IL9R cDNA.

EXAMPLE 7

The sequence of clone p9RC4, presented as SEQ ID NO: 1, shows an open reading frame coding a 468 amino acid protein. The deduced amino acid sequence predicts two hydrophobic regions, one of which spans amino acids 15–40, and probably represents a signal peptide. The probability weight matrix of von Heyne, Nucl. Acids Res. 14: 4683–4690 (1986) predicts a cleavage site for the signal peptide between positions 37 and 39. The second hydrophobic domain spans amino acids 271–291. This is presumed to constitute the transmembrane domain.

The putative extracellular domain contains 233 amino acids, including 6 cysteine residues and two potential N-linked glycosylation sites at positions 116 and 155. A "WSEWS" amino acids 244–248 of SEQ ID No: 7 motif, i.e., "Trp-Ser-Glu-Trp-Ser" amino acids 244–248 of SEQ ID No: 7, typical of the hematopoietin receptor superfamily described by Idzerda et al., J. Exp. Med. 171: 861–873 (1990), is found at positions 244–248.

The cytoplasmic portion of the molecule is characterized by a high percentage of serine (13%), and proline (12.4%), as well as three potential protein kinase C phosphorylation sites at positions 294, 416 and 465.

Comparison of the various clones indicates that p9RA1 and p9RB3 contain an additional glutamine between position 192 and 193 as compared to p9RC4, but without a frameshift. This residue lies in the extracellular domain, but as example 4, supra shows, it does not appear to affect the affinity for ligand. There is a 22 nucleotide deletion at this position in p9RC2. These features, and a potential intronic sequence in p9RC9, suggest alternate splicing events.

The analysis of p9RB3 implies the existence of a soluble form of IL9R. The cDNA for this clone contains a large part of extracellular domain, but lacks nucleotides 651–1719, which code the end of the N-terminal domain, the transmembrane and the cytoplasmic domain.

Clone p9RA1 is different from all other clones in that there is a stop codon after alanine (378), which is followed by a 736 base pair sequence unrelated to any other cDNA's sequenced.

The sequences for the murine CDNA described in this example is provided as follows:

p9RC4 (SEQ ID NO: 1)
p9RA1 (SEQ ID NO: 2)
p9RB3 (SEQ ID NO: 3).

The deduced amino acid sequences encoded by these cDNAs are presented as SEQ ID NOS: 7, 8 and 9 respectively.

EXAMPLE 8

The CDNA for human IL9-R was also analyzed. As indicated supra, clone ph9RA3 showed 66% identity with murine p9RC4 and 53% homology on the amino acid sequence level. A putative cleavage site is positioned between amino acids 39 and 40. This site is conserved between species, as is the transmembrane domain, the two potential N-glycosylation sites, and the consensus sequence for the hematopoietic superfamily, all of which are described in Example 7.

The cytoplasmic portion of the protein seemed less conserved, and was much larger (231 amino acids) than the murine counterpart (177 residues). Due to a stretch of 9 consecutive serines in positions 431–439, there is a high percentage of serine in the molecule (11.2%).

Clones ph9RA2, 4, 6 and 9 confirmed the sequence derived from ph9RA3. The clone ph9RA5, however, has an 85 nucleotide deletion in positions 1063–1147, suggesting a truncated protein. The putative truncated protein would be 307 amino acids long, and contain the complete extracellular and transmembrane regions of IL9-R, 5 amino acids of the cytoplasmic domain, and 11 unrelated residues.

The clone referred to as pH9RA6 contains a short intervening sequence at the beginning of the DNA, which leads into a stop codon, in frame with the normal initiative codon. It also creates a new ATG triplet in frame with the downstream portion of the coding sequence. In the IL9R molecule, this yields a transcript with a unique N-terminal sequence, the rest of the sequence being identical to pH9RA3. Comparison of pH9RA6 and pH9RA3 shows that, after the initial methionine common to both clones, pH9RA6 contains an insert of 22 amino acids. These are followed by the sequence "GWTLESE . . ." amino acids 10–16 of SEQ ID No: 10 which is the sequence beginning at position 10 of pH9RA3.

The nucleic acid sequences for ph9RA3, ph9RA5 and pH9RA6 are presented as SEQ ID NO: 4, SEQ ID NO: 5 and SEQ ID NO: 6, respectively. The deduced amino acid sequences encoded by these are presented as SEQ ID NOS: 10, 11 and 12.

The foregoing teaches the isolation of a nucleic acid sequence which codes for the interleukin-9 receptor. Both murine and the homology found therebetween (53%, with up to 67% in the extracellular region) suggests that nucleic acid sequences coding for IL9-R from other species could also be identified.

The following data deal with CDNA, but it will be seen that the sequences of the cDNA put one in position of mRNA, as the latter can be derived from the former based on well known rules regarding construction of the sequences. Given the cDNA information, it is presumed that one could also secure the genomic analog of the cDNAs.

The information provided herein also teaches construction of vectors, such as plasmids, which contain the nucleic acid sequences of interest, i.e., those coding for mammalian IL9R. Such vectors may contain components in addition to the coding sequence, such as promoters operably linked to the coding sequence, "markers", such as genes for antibiotic resistance or selection, including the thymidine kinase or "TK" gene, as well as others which will be known to the skilled artisan. The nucleic acid sequences and vectors may be used—as has been shown—to transfect various cell types, such as "COS", "CHO", Spodoptera fruaiperda or other insect cell lines. The sequences, either alone or in appropriate vectors, can be used to transfect a panoply of prokaryotic and eukaryotic cells.

The isolation of nucleic acid sequences coding for the IL-9 receptor makes it possible for investigators to carry out several lines of investigation which were not possible or much more difficult without these. For example, as pointed out supra, even on these cells which express it best, expression of IL-9R is low. Isolation of the gene makes it possible to transfect recipient cells, followed by overexpression, amplification, etc. This leads to sufficient expression on cell surfaces to permit immunization with these cells, and generation of an immunogenic response to IL-9R, including the production of antibodies. Isolation of the antibody producing cells, followed by standard techniques of hybridoma biology leads to production of IL-9R specific monoclonal antibodies.

The antibodies produced, be they polyclonal or monoclonal, can then be used in therapeutic methods to block IL-9 from binding to IL-9R molecules. As binding of IL-9 to cell surfaces is implicated in several pathological conditions, this is an important therapeutic goal.

In addition IL-9R specific antibodies can be used for both qualitative and quantitative measurement of IL-9R expression on cells, following known immunoassay protocols.

The examples supra show the existence of a soluble form of IL-9R. As with other soluble interleukin receptor molecules (see Fanslow et al., supra), this molecule can be used to prevent the binding of IL-9 to cell bound receptor, and thus interfere with the affect of IL-9 on a cell type, subpopulation, etc. As such, soluble IL-9R may be said to be an antagonist for IL-9.

Recent work has shown that the soluble form of one interleukin receptor, i.e., IL-6R, functions as an agonist. See Taga et al., Cell 58: 573–591 (Aug. 11, 1989). The soluble form of IL-9R might function in a similar manner. In addition the IL-9R molecule, either the soluble form or a solubilized form of the molecule may be used as an immunogen for generation of IL-9R specific antibodies. Either the entire receptor molecule, or an immunogenic portion thereof, can be used in an appropriate animal, such as a mouse, rabbit or guinea pig, to generate an immune response which includes antibody formation. The antibodies can then be purified using standard techniques. Alternatively, antibody producing B cells can be isolated and utilized in any of the standard methods for producing hybridomas, so as to lead to the generation of IL-9R specific monoclonal antibodies.

An assay is described suDra, in Example 6, in which IL-9R cDNA expression is assayed by measuring the responsiveness of a transfected cell line to IL9. This assay methodology provides a means for screening for various agonists and antagonists. In brief, a transfected cell sample containing a sequence coding for IL9R is contacted with a compound of interest. If the compound is an agonist, it will bind to the IL-9R molecule on the cell surface, and lead to the series of events usually associated with IL-9/IL-9R binding. To the same end, an antagonist can be assayed by combining the compound of interest with IL-9 and the cell sample to determine whether the IL-9 has diminished impact, or no impact. The assay for agonist/antagonist may be viewed as part of a broader invention wherein one may assay for molecules which compete for binding to IL-9R.

In addition to the coding sequences discussed herein, the invention also embraces sequences complementary to the coding sequences. These complements, which can be derived from the coding sequences themselves, may be used, e.g., as probes or as "anti-sense" inhibitors to prevent expression of the IL9R coding sequences. Other aspects of the invention will be clear to the skilled artisan, and do not require elaboration here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A process for producing an antibody which specifically binds to interleukin 9 receptor comprising immunizing a subject animal with a cell line transfected with a nucleic acid molecule which codes for interleukin-9 receptor in an amount sufficient to generate antibodies which specifically bind to interleukin-9 receptor, and isolating said antibodies from said animal.

2. A method for producing an antibody which specifically binds to interleukin 9 receptor comprising immunizing a non-human animal with a non-glycosylated interleukin 9 receptor in an amount sufficient to generate an antibody specific for interleukin 9 receptor, and purifying said antibody.

3. Monoclonal antibody which specifically binds to an interleukin-9 receptor.

4. The monoclonal antibody of claim 3, which specifically binds to human interleukin-9 receptor.

5. Hybridoma cell line which produces the monoclonal antibody of claim 3.

6. Hybridoma cell line which produces the monoclonal antibody of claim 4.

7. The method according to claim 2 wherein the interleukin 9 receptor is a murine interleukin 9 receptor.

8. The method of claim 1, wherein said cell line is eukaryotic.

9. A method for producing an isolated monoclonal antibody which specifically binds to interleukin 9 receptor comprising immunizing a non-human animal with a protein having an amino acid sequence selected from the group consisting of SEQ ID NO.: 7, 8, 9, 10, 11, and 12, in an amount sufficient to generate a monoclonal antibody specific for interleukin 9 receptor.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 2281 base pairs
      (B) TYPE: nucleic acid
      (C) STRANDEDNESS: single
      (D) TOPOLOGY: linear (xi) SEQUENCE DESCRIPTION: SEQ ID NO: 1:

```
CTCCATGGCC CTGGGAAGAT GCATTGCGGA AGGTTGGACC TTGGAGAGAG TGGCGGTGAA        60

ACAGGTCTCC TGGTTCCTGA TCTACAGCTG GGTCTGCTCT GGAGTCTGCC GGGGAGTCTC       120

GGTCCCAGAG CAAGGAGGAG GAGGGCAGAA GGCTGGAGCA TTCACCTGTC TCAGCAACAG       180

TATTTACAGG ATCGACTGCC ACTGGTCGGC TCCAGAGCTG GGCCAGGAAT CCAGGGCCTG       240

GCTCCTCTTT ACCAGTAACC AGGTGACTGA AATCAAACAC AAATGCACCT TCTGGGACAG       300

TATGTGTACC CTGGTGCTGC CTAAAGAGGA GGTGTTCTTA CCTTTTGACA ACTTCACCAT       360

CACACTTCAC CGCTGCATCA TGGGACAGGA ACAGGTCAGC CTGGTGGACT CACAGTACCT       420

GCCCAGGAGA CACATCAAGT TGGACCCACC CTCTGATCTG CAGAGCAATG TCAGCTCTGG       480

GCGTTGTGTC CTGACCTGGG GTATCAATCT TGCCCTGGAG CCATTGATCA CATCCCTCAG       540

CTACGAGCTG GCCTTCAAGA GGCAGGAAGA GGCCTGGGAG GCCCGGCACA AGGACCGTAT       600

CGTTGGAGTG ACCTGGCTCA TCCTTGAAGC CGTCGAACTG AATCCTGGTT CCATCTACGA       660

GGCCAGGCTG CGTGTCCAGA TGACTTTGGA GAGTTATGAG GACAAGACAG AGGGGGAATA       720

TTATAAGAGC CATTGGAGTG AGTGGAGCCA GCCCGTGTCC TTTCCTTCTC CCCAGAGGAG       780
```

```
ACAGGGCCTC CTGGTCCCAC GCTGGCAATG GTCAGCCAGC ATCCTTGTAG TTGTGCCCAT      840

CTTTCTTCTG CTGACTGGCT TTGTCCACCT TCTGTTCAAG CTGTCACCCA GGCTGAAGAG      900

AATCTTTTAC CAGAACATTC CATCTCCCGA GGCGTTCTTC CATCCTCTCT ACAGTGTGTA      960

CCATGGGGAC TTCCAGAGTT GGACAGGGGC CCGCAGAGCC GGACCACAAG CAAGACAGAA     1020

TGGTGTCAGT ACTTCATCAG CAGGCTCAGA GTCCAGCATC TGGGAGGCCG TCGCCACACT     1080

CACCTATAGC CCGGCATGCC CTGTGCAGTT TGCCTGCCTG AAGTGGGAGG CCACAGCCCC     1140

GGGCTTCCCA GGGCTCCCAG GCTCAGAGCA TGTGCTGCCG GCAGGGTGTC TGGAGTTGGA     1200

AGGACAGCCA TCTGCCTACC TGCCCCAGGA GGACTGGGCC CCACTGGGCT CTGCCAGGCC     1260

CCCTCCTCCA GACTCAGACA GCGGCAGCAG CGACTATTGC ATGTTGGACT GCTGTGAGGA     1320

ATGCCACCTC TCAGCCTTCC CAGGACACAC CGAGAGTCCT GAGCTCACGC TAGCTCAGCC     1380

TGTGGCCCTT CCTGTGTCCA GCAGGGCCTG ACACCTACCA AGGGATGTGG GCATTCTCTT     1440

CCCTCCTATC CTCGGATGGC ACCAGACACA GTCTCTGCGT GTCTCTGCTA GGTGCACCAT     1500

GTCTGTTTTG GGGAGATGAA CGAAAGGCCC CAGGCTGACC CTGGGGTGCG TGTGGAACTC     1560

CGGAGAGGAG GCAGCTGTGC ACGGATCAGA GGCAATGCGG ATGGAAGCAG TAGACTGTGC     1620

CTTACCCCCC TGCTCTGCCT TTGTGGTGGG GATGCCTCCA GGGTCAGCAT CTTAACATCG     1680

CCTTCGCTTC TCTTGTCTTT CTGGCTCTGT CCCAGGCCTG AAAAAAGAAT GTGACAAGCA     1740

GCCTGGTCTG TTCTTCCACC CCTAAAGGGC TGGCCTGGGC CAGGGACAC TGATGAGACA      1800

ACATTGGTGA AGTGTCCCTT TTCAGTGCCT TTCCCATTAA GACCAGAAGG GACGCTTTTG     1860

ACTGCAGGCT GTGGGTGGCT GGGTACGAG GGAATGATGG AGCTTTGAGC AGGTGGGGTT      1920

GTCCATCTTT GAGCTTTTGG GGTTCCAAGA TCAGCTGGAA GGAGTCTCAC CGACTGATTC     1980

AAAGAAGTCT TACCCATCTG TGATATTTTC TTTCCTGGTG CCGTGATAAA ACACCGTGAC     2040

CAAAAATGAC TTACAAAAGG AAGAGTTGGC TTGGTTTAAG GTTCCAGAGG TGTGGAGACA     2100

TGGCAGCCAG CGGCACACAT GGCAGTGAGG ACAGGAAGCT GAGAGCTCAC ATCTCAACCA     2160

AAAGTTGAGT GAACTGAAAG TACTATCCCC TCCCCCACCC CAACTCCAGC AAGGCTCCAC     2220

CCCCCTGAAG GTTCCATGCC TCCCTAAACA GCTCGGCCAA ATAGAGACCA AGTGTTCAAA     2280

T                                                                    2281
```

(2) INFORMATION FOR SEQ ID NO: 2:

(i) SEQUENCE CHARACTERISTICS:
        (A) LENGTH: 1905 base pairs
        (B) TYPE: nucleic acid
        (C) STRANDEDNESS: single
        (D) TOPOLOGY: linear (xi) SEQUENCE DESCRIPTION: SEQ ID NO: 2:

```
CACCTCCTGG CTGGGGCTGC CTGAGACTCT CCATGGCCCT GGGAAGATGC ATTGCGGAAG       60

GTTGGACCTT GGAGAGAGTG GCGGTGAAAC AGGTCTCCTG GTTCCTGATC TACAGCTGGG      120

TCTGCTCTGG AGTCTGCCGG GGAGTCTCGG TCCCAGAGCA AGGAGGAGGA GGGCAGAAGG      180

CTGGAGCATT CACCTGTCTC AGCAACAGTA TTTACAGGAT CGACTGCCAC TGGTCGGCTC      240

CAGAGCTGGG CCAGGAATCC AGGGCCTGGC TCCTCTTTAC CAGTAACCAG GTGACTGAAA      300

TCAAACACAA ATGCACCTTC TGGGACAGTA TGTGTACCCT GGTGCTGCCT AAAGAGGAGG      360

TGTTCTTACC TTTTGACAAC TTCACCATCA CACTTCACCG CTGCATCATG GGACAGGAAC      420

AGGTCAGCCT GGTGGACTCA CAGTACCTGC CCAGGAGACA CATCAAGTTG GACCCACCCT      480
```

-continued

```
CTGATCTGCA GAGCAATGTC AGCTCTGGGC GTTGTGTCCT GACCTGGGGT ATCAATCTTG    540

CCCTGGAGCC ATTGATCACA TCCCTCAGCT ACGAGCTGGC CTTCAAGAGG CAGGAAGAGG    600

CCTGGGAGCA GGCCCGGCAC AAGGACCGTA TCGTTGGAGT GACCTGGCTC ATCCTTGAAG    660

CCGTCGAACT GAATCCTGGT TCCATCTACG AGGCCAGGCT GCGTGTCCAG ATGACTTTGG    720

AGAGTTATGA GGACAAGACA GAGGGGGAAT ATTATAAGAG CCATTGGAGT GAGTGGAGCC    780

AGCCCGTGTC CTTTCCTTCT CCCCAGAGGA GACAGGGCCT CCTGGTCCCA CGCTGGCAAT    840

GGTCAGCCAG CATCCTTGTA GTTGTGCCCA TCTTTCTTCT GCTGACTGGC TTTGTCCACC    900

TTCTGTTCAA GCTGTCACCC AGGCTGAAGA GAATCTTTTA CCAGAACATT CCATCTCCCG    960

AGGCGTTCTT CCATCCTCTC TACAGTGTGT ACCATGGGGA CTTCCAGAGT TGGACAGGGG   1020

CCCGCAGAGC CGGACCACAA GCAAGACAGA ATGGTGTCAG TACTTCATCA GCAGGCTCAG   1080

AGTCCAGCAT CTGGGAGGCC GTCGCCACAC TCACCTATAG CCCGGCATGC CCTGTGCAGT   1140

TTGCCTGCCT GAAGTGGGAG GCCACAGCGT GAGAAGGGAC AGCCAGCCAC TCAGTGCGTG   1200

GGCTTAGATT GGGAAGAGAC CTCCCAAGCA GCTTCCCCTC CTCCCCAGCC CCTGCCATTC   1260

ACCCCTGCTG GCCGTCCATC CCCAGGATCC ACTGTGGAGC CAAGCCCACA GACCCGGCCT   1320

GATTCAGCTC TGACACTCGC TGCGCTGCTC CGTTGTGAAC TTTGGCCAAG TCACCACTTT   1380

TACCTCAGCT TCCTCCTGTG AGAACAGGGT TGCCTTAGAG TTGCCTAATC CCTAAGGAGA   1440

CTGAGACAAA CTTGTCTGCA AATATCTATC CGATGTATAT TGTTAGGAGC TCGAGGGTCC   1500

GTGGGTGGGC GGGGCAGGGG GGTGGGGATG CGGTTGGCGC ATATCACTGT GTCAACAGCC   1560

AGAGCCTTCC TCCATGTCTC AACCAACACT CTCCAAGCTG AATTCTCAGG CTGAACTCAC   1620

TGTCACCTGT GAAGTAAACC CCGGCAGACC TGGAAGATTG GTGGTAGGAT TGTGGAGGTT   1680

GCAGGGAGCA TGCTCAGTGG GCACTAGTTG CCTGCTGGGT ACCAGGAGAT GCTTGTGCCC   1740

TGAGGTATCT TTAAGAACTA TCACGGAATT GGACTGGGAG CTCAGGAGAG AGCTTGGTAG   1800

ACTGGCAGTG TCAGTGAAAC AGTTATTTAG CCAAGAACAA CATTCCTGGG GCTGGGGACA   1860

GTGGCTCGGT GAAACCAACC TGGAACATGG GAGGTTGTAA GTTCG                  1905
```

(2) INFORMATION FOR SEQ ID NO: 3:

(i) SEQUENCE CHARACTERISTICS:
        (A) LENGTH: 1214 base pairs
        (B) TYPE: nucleic acid
        (C) STRANDEDNESS: single
        (D) TOPOLOGY: linear (xi) SEQUENCE DESCRIPTION: SEQ ID NO: 3:

```
ATGGCCCTGG GAAGATGCAT TGCGGAAGGT TGGACCTTGG AGAGAGTGGC GGTGAAACAG     60

GTCTCCTGGT TCCTGATCTA CAGCTGGGTC TGCTCTGGAG TCTGCCGGGG AGTCTCGGTC    120

CCAGAGCAAG GAGGAGGAGG GCAGAAGGCT GGAGCATTCA CCTGTCTCAG CAACAGTATT    180

TACAGGATCG ACTGCCACTG GTCGGCTCCA GAGCTGGGCC AGGAATCCAG GGCCTGGCTC    240

CTCTTTACCA GTAACCAGGT GACTGAAATC AAACACAAAT GCACCTTCTG GGACAGTATG    300

TGTACCCTGG TGCTGCCTAA AGAGGAGGTG TTCTTACCTT TTGACAACTT CACCATCACA    360

CTTCACCGCT GCATCATGGG ACAGGAACAG GTCAGCCTGG TGGACTCACA GTACCTGCCC    420

AGGAGACACA TCAAGTTGGA CCCACCCTCT GATCTGCAGA GCAATGTCAG CTCTGGGCGT    480

TGTGTCCTGA CCTGGGGTAT CAATCTTGCC CTGGAGCCAT TGATCACATC CCTCAGCTAC    540

GAGCTGGCCT TCAAGAGGCA GGAAGAGGCC TGGGAGCAGG CCCGGCACAA GGACCGTATC    600

GTTGGAGTGA CCTGGCTCAT CCTTGAAGCC GTCGAACTGA ATCCTGAAAA AGAATGTGA    660
```

| | |
|---|---|
| CAAGCAGCCT GGTCTGTTCT TCCACCCCTA AAGGGCTGGC CTGGGCCCAG GGACACTGAT | 720 |
| GAGACAACAT TGGTGAAGTG TCCCTTTTCA GTGCCTTTCC CATTAAGACC AGAAGGGACG | 780 |
| CTTTTGACTG CAGGCTGTGG GTGGCTGGGT ACGGAGGGAA TGATGGAGCT TTGAGCAGGT | 840 |
| GGGGTTGTCC ATCTTTGAGC TTTTGGGTTC CAAGATCAGC TGGAAGGAGT CTCACCGACT | 900 |
| GATTCAAAGA AGTCTTACCC ATCTGTGATA TTTTCTTTCC TGGTGCCGTG ATAAAACACC | 960 |
| GTGACCAAAA ATGACTTACA AAAGGAAGAG TTGGCTTGGT TTAAGGTTCC AGAGGTGTGG | 1020 |
| AGACATGGCA GCCAGCGGCA CACATGGCAG TGAGGACAGG AAGCTGAGAG CTCACATCTC | 1080 |
| AACCAAAAGT TGAGTGAACT GAAAGTACTA TCCCCTCCCC CACCCCAACT CCAGCAAGGC | 1140 |
| TCCACCCCCC TGAAGGTTCC ATGCCTCCCT AAACAGCTCG GCCAAATAGA GACCAAGTGT | 1200 |
| TCAAATAAAA AAAA | 1214 |

(2) INFORMATION FOR SEQ ID NO: 4:

(i) SEQUENCE CHARACTERISTICS:
        (A) LENGTH: 1947 base pairs
        (B) TYPE: nucleic acid
        (C) STRANDEDNESS: single
        (D) TOPOLOGY: linear (xi) SEQUENCE DESCRIPTION: SEQ ID NO: 4:

| | |
|---|---|
| AGCAGCTCTG TAATGCGCTT GTGGTTTCAG ATGTGGGCGG CCTGTGTGAA CCTGTCGTGC | 60 |
| AAAGCTCACG TCACCAACTG CTGCAGTTAT CTCCTGAATC AGGCTGAGGG TCTTTGCTGT | 120 |
| GCACCCAGAG ATAGTTGGGT GACAAATCAC CTCCAGGTTG GGGATGCCTC AGACTTGTGA | 180 |
| TGGGACTGGG CAGATGCATC TGGGAAGGCT GGACCTTGGA GAGTGAGGCC CTGAGGCGAG | 240 |
| ACATGGGCAC CTGGCTCCTG GCCTGCATCT GCATCTGCAC CTGTGTCTGC TTGGGAGTCT | 300 |
| CTGTCACAGG GGAAGGACAA GGGCCAAGGT CTAGAACCTT CACCTGCCTC ACCAACAACA | 360 |
| TTCTCAGGAT CGATTGCCAC TGGTCTGCCC CAGAGCTGGG ACAGGGCTCC AGCCCCTGGC | 420 |
| TCCTCTTCAC CAGCAACCAG GCTCCTGGCG GCACACATAA GTGCATCTTG CGGGGCAGTG | 480 |
| AGTGCACCGT CGTGCTGCCA CCTGAGGCAG TGCTCGTGCC ATCTGACAAT TCACCATCA | 540 |
| CTTTCCACCA CTGCATGTCT GGGAGGGAGC AGGTCAGCCT GGTGGACCCG GAGTACCTGC | 600 |
| CCCGGAGACA CGTTAAGCTG GACCCGCCCT CTGACTTGCA GAGCAACATC AGTTCTGGCC | 660 |
| ACTGCATCCT GACCTGGAGC ATCAGTCCTG CCTTGGAGCC AATGACCACA CTTCTCAGCT | 720 |
| ATGAGCTGGC CTTCAAGAAG CAGGAAGAGG CCTGGGAGCA GGCCCAGCAC AGGGATCACA | 780 |
| TTGTCGGGGT GACCTGGCTT ATACTTGAAG CCTTTGAGCT GGACCCTGGC TTTATCCATG | 840 |
| AGGCCAGGCT GCGTGTCCAG ATGGCCACAC TGGAGGATGA TGTGGTAGAG GAGGAGCGTT | 900 |
| ATACAGGCCA GTGGAGTGAG TGGAGCCAGC CTGTGTGCTT CCAGGCTCCC CAGAGACAAG | 960 |
| GCCCTCTGAT CCCACCCTGG GGGTGGCCAG GCAACACCCT TGTTGCTGTG TCCATCTTTC | 1020 |
| TCCTGCTGAC TGGCCCGACC TACCTCCTGT TCAAGCTGTC GCCCAGGGTG AAGAGAATCT | 1080 |
| TCTACCAGAA CGTGCCCTCT CCAGCGATGT TCTTCCAGCC CCTCTACAGT GTACACAATG | 1140 |
| GGAACTTCCA GACTTGGATG GGGGCCCACA GGGCCGGTGT GCTGTTGAGC CAGGACTGTG | 1200 |
| CTGGCACCCC ACAGGGAGCC TTGGAGCCCT GCGTCCAGGA GGCCACTGCA CTGCTCACTT | 1260 |
| GTGGCCCAGC GCGTCCTTGG AAATCTGTGG CCCTGGAGGA GGAACAGGAG GGCCCTGGGA | 1320 |
| CCAGGCTCCC GGGGAACCTG AGCTCAGAGG ATGTGCTGCC AGCAGGGTGT ACGGAGTGGA | 1380 |
| GGGTACAGAC GCTTGCCTAT CTGCCACAGG AGGACTGGGC CCCCACGTCC CTGACTAGGC | 1440 |

| | | | | |
|---|---|---|---|---|
| CGGCTCCCCC | AGACTCAGAG | GGCAGCAGGA | GCAGCAGCAG | CAGCAGCAGC AGCAGCAACA | 1500 |
| ACAACAACTA | CTGTGCCTTG | GGCTGCTATG | GGGGATGGCA | CCTCTCAGCC CTCCCAGGAA | 1560 |
| ACACACAGAG | CTCTGGGCCC | ATCCCAGCCC | TGGCCTGTGG | CCTTTCTTGT GACCATCAGG | 1620 |
| GCCTGGAGAC | CCAGCAAGGA | GTTGCCTGGG | TGCTGGCTGG | TCACTGCCAG AGGCCTGGGC | 1680 |
| TGCATGAGGA | CCTCCAGGGC | ATGTTGCTCC | CTTCTGTCCT | CAGCAAGGCT CGGTCCTGGA | 1740 |
| CATTCTAGGT | CCCTGACTCG | CCAGATGCAT | CATGTCCATT | TTGGGAAAAT GGACTGAAGT | 1800 |
| TTCTGGAGCC | CTTGTCTGAG | ACTGAACCTC | CTGAGAAGGG | GCCCCTAGCA GCGGTCAGAG | 1860 |
| GTCCTGTCTG | GATGGAGGCT | GGAGGCTCCC | CCCTCAACCC | CTCTGCTCAG TGCCTGTGGG | 1920 |
| GAGCAGCCTC | TACCCTCAGC | ATCCTGG | | | 1947 |

(2) INFORMATION FOR SEQ ID NO: 5:

(i) SEQUENCE CHARACTERISTICS:
        (A) LENGTH: 1683 base pairs
        (B) TYPE: nucleic acid
        (C) STRANDEDNESS: single
        (D) TOPOLOGY: linear (xi) SEQUENCE DESCRIPTION: SEQ ID NO: 5:

| | | | | |
|---|---|---|---|---|
| ATGGGACTGG | GCAGATGCAT | CTGGGAAGGC | TGGACCTTGG | AGAGTGAGGC CCTGAGGCGA | 60 |
| GACATGGGCA | CCTGGCTCCT | GGCCTGCATC | TGCATCTGCA | CCTGTGTCTG CTTGGGAGTC | 120 |
| TCTGTCACAG | GGGAAGGACA | AGGGCCAAGG | TCTAGAACCT | TCACCTGCCT CACCAACAAC | 180 |
| ATTCTCAGGA | TCGATTGCCA | CTGGTCTGCC | CCAGAGCTGG | ACAGGGCTC CAGCCCCTGG | 240 |
| CTCCTCTTCA | CCAGCAACCA | GGCTCCTGGC | GGCACACATA | AGTGCATCTT GCGGGGCAGT | 300 |
| GAGTGCACCG | TCGTGCTGCC | ACCTGAGGCA | GTGCTCGTGC | CATCTGACAA TTTCACCATC | 360 |
| ACTTTCCACC | ACTGCATGTC | TGGGAGGGAG | CAGGTCAGCC | TGGTGGACCC GGAGTACCTG | 420 |
| CCCCGGAGAC | ACGTTAAGCT | GGACCCGCCC | TCTGACTTGC | AGAGCAACAT CAGTTCTGGC | 480 |
| CACTGCATCC | TGACCTGGAG | CATCAGTCCT | GCCTTGGAGC | CAATGACCAC ACTTCTCAGC | 540 |
| TATGAGCTGG | CCTTCAAGAA | GCAGGAAGAG | GCCTGGGAGC | AGGCCCAGCA CAGGGATCAC | 600 |
| ATTGTCGGGG | TGACCTGGCT | TATACTTGAA | GCCTTTGAGC | TGGACCCTGG CTTTATCCAT | 660 |
| GAGGCCAGGC | TGCGTGTCCA | GATGGCCACA | CTGGAGGATG | ATGTGGTAGA GGAGGAGCGT | 720 |
| TATACAGGCC | AGTGGAGTGA | GTGGAGCCAG | CCTGTGTGCT | TCCAGGCTCC CCAGAGACAA | 780 |
| GGCCCTCTGA | TCCCACCCTG | GGGGTGGCCA | GGCAACACCC | TTGTTGCTGT GTCCATCTTT | 840 |
| CTCCTGCTGA | CTGGCCCGAC | CTACCTCCTG | TTCAAGCTGT | CGCCCAGACT TGGATGGGGG | 900 |
| CCCACAGGGC | CGGTGTGCTG | TTGAGCCAGG | ACTGTGCTGG | CACCCACAG GGAGCCTTGG | 960 |
| AGCCCTGCGT | CCAGGAGGCC | ACTGCACTGC | TCACTTGTGG | CCCAGCGCGT CCTTGGAAAT | 1020 |
| CTGTGGCCCT | GGAGGAGGAA | CAGGAGGGCC | CTGGGACCAG | GCTCCCGGGG AACCTGAGCT | 1080 |
| CAGAGGATGT | GCTGCCAGCA | GGGTGTACGG | AGTGGAGGGT | ACAGACGCTT GCCTATCTGC | 1140 |
| CACAGGAGGA | CTGGGCCCCC | ACGTCCCTGA | CTAGGCCGGC | TCCCCAGAC TCAGAGGGCA | 1200 |
| GCAGGAGCAG | CAGCAGCAGC | AGCAGCAGCA | GCAACAACAA | CAACTACTGT GCCTTGGGCT | 1260 |
| GCTATGGGGG | ATGGCACCTC | TCAGCCCTCC | CAGGAAACAC | ACAGAGCTCT GGGCCCATCC | 1320 |
| CAGCCCTGGC | CTGTGGCCTT | TCTTGTGACC | ATCAGGGCCT | GGAGACCCAG CAAGGAGTTG | 1380 |
| CCTGGGTGCT | GGCTGGTCAC | TGCCAGAGGC | CTGGGCTGCA | TGAGGACCTC CAGGGCATGT | 1440 |
| TGCTCCCTTC | TGTCCTCAGC | AAGGCTCGGT | CCTGGACATT | CTAGGTCCCT GACTCGCCAG | 1500 |
| ATGCATCATG | TCCATTTTGG | GAAAATGGAC | TGAAGTTTCT | GGAGCCCTTG TCTGAGACTG | 1560 |

```
AACCTCCTGA AAGGGGCCCC CTAGCAGCGG TCAGAGGTCC TGTCTGGATG GAGGCTGGAG      1620

GCTCCCCCCT CAACCCCTCT GCTCAGTGCC TGTGGGAGC AGCCTCTACC CTCAGCATCC       1680

TGG                                                                    1683

(2) INFORMATION FOR SEQ ID NO: 6:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (xi) SEQUENCE DESCRIPTION: SEQ ID NO: 6:

CCAGGTTGGG GATGCCTCAG ACTTGTGATG GGACTGGGCA GATGCATCTG GAAGGTCCT        60

GGTGGTGACT CCAACCCTGC CCTCACATAT CCCAAGAGCA GCTGACTGCG CTTCCCCATT      120

CCCACCTTTC CAGTAACTGC TGCAAGAACG GACAGACACT GCTGCAGAGA ACTTGCCACG      180

GTGTTTCATG CTGTGGCTGG TGGTTCCAGG CTGCACGCTC CATTCTAGGA AAGGGGCCCT      240

CAGCCAGTCC CTTGCAGGCT GGACCTTGGA GAGTGAGGCC CTGAGGCGAG ACATGGGCAC      300

CTGGCTCCTG GCCTGCATCT GCATCTGCAC CTGTGTCTGC TTGGGAGTCT CTGTCACAGG      360

GGAAGGACAA GGGCCAAGGT CTAGAACCTT CACCTGCCTC ACCAACAACA TTCTCAGGAT      420

CGATTGCCAC TGGTCTGCCC CAGAGCTGGG ACAGGGCTCC AGCCCCTGGC TCCTCTTCAC      480

CAGCAACCAG GCTCCTGGCG GCACACATAA GTGCATCTTG CGGGGCAGTG AGTGCACCGT      540

CGTGCTGCCA CCTGAGGCAG TGCTCGTGCC ATCTGACAAT TTCACCATCA CTTTCCACCA      600

CTGCATGTCT GGGAGGGAGC AGGTCAGCCT GGTGGACCCG GAGTACCTGC CCCGGAGACA      660

CGTTAAGCTG GACCCGCCCT CTGACTTGCA GAGCAACATC AGTTCTGGCC ACTGCATCCT      720

GACCTGGAGC ATCAGTCCTG CCTTGGAGCC AATGACCACA CTTCTCAGCT ATGAGCTGGC      780

CTTCAAGAAG CAGGAAGAGG CCTGGGAGCA GGCCCAGCAC AGGGATCACA TTGTCGGGGT      840

GACCTGGCTT ATACTTGAAG CCTTTGAGCT GGACCCTGGC TTTATCCATG AGGCCAGGCT      900

GCGTGTCCAG ATGGCCACAC TGGAGGATGA TGTGGTAGAG GAGGAGCGTT ATACAGGCCA      960

GTGGAGTGAG TGGAGCCAGC CTGTGTGCTT CCAGGCTCCC CAGAGACAAG GCCCTCTGAT     1020

CCCACCCTGG GGGTGGCCAG GCAACACCCT TGTTGCTGTG TCCATCTTTC TCCTGCTGAC     1080

TGGCCCGACC TACCTCCTGT TCAAGCTGTC GCCCAGGGTG AAGAGAATCT TCTACCAGAA     1140

CGTGCCCTCT CCAGCGATGT TCTTCCAGCC CCTCTACAGT GTACACAATG GAACTTCCA      1200

GACTTGGATG GGGGCCCACA GGGCCGGTGT GCTGTTGAGC CAGGACTGTG CTGGCACCCC     1260

ACAGGGAGCC TTGGAGCCCT GCGTCCAGGA GGCCACTGCA CTGCTCACTT GTGGCCCAGC     1320

GCGTCCTTGG AAATCTGTGG CCCTGGAGGA GGAACAGGAG GGCCCTGGGA CCAGGCTCCC     1380

GGGGAACCTG AGCTCAGAGG ATGTGCTGCC AGCAGGGTGT ACGGAGTGGA GGGTACAGAC     1440

GCTTGCCTAT CTGCCACAGG AGGACTGGGC CCCCACGTCC CTGACTAGGC CGGCTCCCCC     1500

AGACTCAGAG GGCAGCAGGA GCAGCAGCAG CAGCAGCAGC AGCAGCAACA ACAACAACTA     1560

CTGTGCCTTG GGCTGCTATG GGGGATGGCA CCTCTCAGCC CTCCCAGGAA ACACACAGAG     1620

CTCTGGGCCC ATCCCAGCCC TGGCCTGTGG CCTTTCTTGT GACCATCAGG GCCTGGAGAC     1680

CCAGCAAGGA GTTGCCTGGG TGCTGGCTGG TCACTGCCAG AGGCCTGGGC TGCATGAGGA     1740

CCTCCAGGGC ATGTTGCTCC CTTCTGTCCT CAGCAAGGCT CGGTCCTGGA CATTCTAGGT     1800

CCCTGACTCG CCAGATGCAT CATGTCCATT TTGGGAAAAT GGACTGAAGT TTCTGGAGCC     1860
```

-continued

```
CTTGTCTGAG ACTGAACCTC CTGAGAAGGG GCCCCTAGCA GCGGTCAGAG GTCCTGTCTG    1920

GATGGAGGCT GGAGGCTCCC CCCTCAACCC CTCTGCTCAG TGCCTGTGGG GAGCAGCCTC    1980

TACCCTCAGC ATCCTGG                                                    1997
```

(2) INFORMATION FOR SEQ ID NO: 7:

(i) SEQUENCE CHARACTERISTICS:
        (A) LENGTH: 468 amino acid residues
        (B) TYPE: amino acid
        (D) TOPOLOGY: linear (xi) SEQUENCE DESCRIPTION: SEQ ID NO: 7:

```
Met Ala Leu Gly Arg Cys Ile Ala Glu Gly Trp Thr Leu Glu Arg Val
                  5                  10                  15

Ala Val Lys Gln Val Ser Trp Phe Leu Ile Tyr Ser Trp Val Cys Ser
             20                  25                  30

Gly Val Cys Arg Gly Val Ser Val Pro Glu Gln Gly Gly Gly Gln
         35                  40                  45

Lys Ala Gly Ala Phe Thr Cys Leu Ser Asn Ser Ile Tyr Arg Ile Asp
 50                  55                  60

Cys His Trp Ser Ala Pro Glu Leu Gly Gln Glu Ser Arg Ala Trp Leu
 65                  70                  75                  80

Leu Phe Thr Ser Asn Gln Val Thr Glu Ile Lys His Lys Cys Thr Phe
                 85                  90                  95

Trp Asp Ser Met Cys Thr Leu Val Leu Pro Phe Glu Val Phe Leu
                100                 105                 110

Pro Phe Asp Asn Phe Thr Ile Thr Leu His Arg Cys Ile Met Gly Gln
            115                 120                 125

Glu Gln Val Ser Leu Val Asp Ser Gln Tyr Leu Pro Arg Arg His Ile
130                 135                 140

Lys Leu Asp Pro Pro Ser Asp Leu Gln Ser Asn Val Ser Ser Gly Arg
145                 150                 155                 160

Cys Val Leu Thr Trp Gly Ile Asn Leu Ala Leu Glu Pro Leu Ile Thr
                165                 170                 175

Ser Leu Ser Tyr Glu Leu Ala Phe Lys Arg Gln Glu Glu Ala Trp Glu
            180                 185                 190

Ala Arg His Lys Asp Arg Ile Val Gly Val Thr Trp Leu Ile Leu Glu
        195                 200                 205

Ala Val Glu Leu Asn Pro Gly Ser Ile Tyr Glu Ala Arg Leu Arg Val
    210                 215                 220

Gln Met Thr Leu Glu Ser Tyr Glu Asp Lys Thr Glu Gly Glu Tyr Tyr
225                 230                 235                 240

Lys Ser His Trp Ser Glu Trp Ser Gln Pro Val Ser Phe Pro Ser Pro
                245                 250                 255

Gln Arg Arg Gln Gly Leu Leu Val Pro Arg Trp Gln Trp Ser Ala Ser
            260                 265                 270

Ile Leu Val Val Val Pro Ile Phe Leu leu Leu Thr Gly Phe Val His
        275                 280                 285

Leu Leu Phe Lys Leu Ser Pro Arg Leu Lys Arg Ile Phe Tyr Gln Asn
    290                 295                 300

Ile Pro Ser Pro Glu Ala Phe Phe His Pro Leu Tyr Ser Val Tyr His
305                 310                 315                 320

Gly Asp Phe Gln Ser Trp Thr Gly Ala Arg Arg Ala Gly Pro Gln Ala
                325                 330                 335
```

```
Arg Gln Asn Gly Val Ser Thr Ser Ala Gly Ser Glu Ser Ser Ile
            340                 345                 350

Trp Glu Ala Val Ala Thr Leu Thr Tyr Ser Pro Ala Cys Pro Val Gln
            355                 360                 365

Phe Ala Cys Leu Lys Trp Glu Ala Thr Ala Pro Gly Phe Pro Gly Leu
    370                 375                 380

Pro Gly Ser Glu His Val Leu Pro Ala Gly Cys Leu Glu Leu Glu Gly
385                 390                 395                 400

Gln Pro Ser Ala Tyr Leu Pro Gln Glu Asp Trp Ala Pro Leu Gly Ser
                405                 410                 415

Ala Arg Pro Pro Pro Asp Ser Asp Ser Gly Ser Ser Asp Tyr Cys
                420                 425                 430

Met Leu Asp Cys Cys Glu Glu Cys His Leu Ser Ala Phe Pro Gly His
            435                 440                 445

Thr Glu Ser Pro Glu Leu Thr Leu Ala Gln Pro Val Ala Leu Pro Val
    450                 455                 460

Ser Ser Arg Ala
465
```

(2) INFORMATION FOR SEQ ID NO: 8:

(i) SEQUENCE CHARACTERISTICS:
        (A) LENGTH: 379 amino acid residues
        (B) TYPE: amino acid
        (D) TOPOLOGY: linear (xi) SEQUENCE DESCRIPTION: SEQ ID NO: 8:

```
Met Ala Leu Gly Arg Cys Ile Ala Glu Gly Trp Thr Leu Glu Arg Val
                5                   10                  15

Ala Val Lys Gln Val Ser Trp Phe Leu Ile Tyr Ser Trp Val Cys Ser
            20                  25                  30

Gly Val Cys Arg Gly Val Ser Val Pro Glu Gln Gly Gly Gly Gly Gln
        35                  40                  45

Lys Ala Gly Ala Phe Thr Cys Leu Ser Asn Ser Ile Tyr Arg Ile Asp
    50                  55                  60

Cys His Trp Ser Ala Pro Glu Leu Gly Gln Glu Ser Arg Ala Trp Leu
65                  70                  75                  80

Leu Phe Thr Ser Asn Gln Val Thr Glu Ile Lys His Lys Cys Thr Phe
                85                  90                  95

Trp Asp Ser Met Cys Thr Leu Val Leu Pro Phe Glu Glu Val Phe Leu
            100                 105                 110

Pro Phe Asp Asn Phe Thr Ile Thr Leu His Arg Cys Ile Met Gly Gln
        115                 120                 125

Glu Gln Val Ser Leu Val Asp Ser Gln Tyr Leu Pro Arg Arg His Ile
    130                 135                 140

Lys Leu Asp Pro Pro Ser Asp Leu Gln Ser Asn Val Ser Ser Gly Arg
145                 150                 155                 160

Cys Val Leu Thr Trp Gly Ile Asn Leu Ala Leu Glu Pro Leu Ile Thr
                165                 170                 175

Ser Leu Ser Tyr Glu Leu Ala Phe Lys Arg Gln Glu Glu Ala Trp Glu
            180                 185                 190

Gln Ala Arg His Lys Asp Arg Ile Val Gly Val Thr Trp Leu Ile Leu
        195                 200                 205

Glu Ala Val Glu Leu Asn Pro Gly Ser Ile Tyr Glu Ala Arg Leu Arg
    210                 215                 220
```

```
Val Gln Met Thr Leu Glu Ser Tyr Glu Asp Lys Thr Glu Gly Glu Tyr
225                 230                 235                 240

Tyr Lys Ser His Trp Ser Glu Trp Ser Gln Pro Val Ser Phe Pro Ser
                245                 250                 255

Pro Gln Arg Arg Gln Gly Leu Leu Val Pro Arg Trp Gln Trp Ser Ala
            260                 265                 270

Ser Ile Leu Val Val Pro Ile Phe Leu Leu Leu Thr Gly Phe Val
        275                 280                 285

His Leu Leu Phe Lys Leu Ser Pro Arg Leu Lys Arg Ile Phe Tyr Gln
    290                 295                 300

Asn Ile Pro Ser Pro Glu Ala Phe Phe His Pro Leu Tyr Ser Val Tyr
305                 310                 315                 320

His Gly Asp Phe Gln Ser Trp Thr Gly Ala Arg Arg Ala Gly Pro Gln
                325                 330                 335

Ala Arg Gln Asn Gly Val Ser Thr Ser Ser Ala Gly Ser Glu Ser Ser
            340                 345                 350

Ile Trp Glu Ala Val Ala Thr Leu Thr Tyr Ser Pro Ala Cys Pro Val
        355                 360                 365

Gln Phe Ala Cys Leu Lys Trp Glu Ala Thr Ala
370                 375
```

(2) INFORMATION FOR SEQ ID NO: 9:

(i) SEQUENCE CHARACTERISTICS:

(A) LENGTH: 219 amino acid residues
        (B) TYPE: amino acid
        (D) TOPOLOGY: linear (xi) SEQUENCE DESCRIPTION: SEQ ID NO: 9:

```
Met Ala Leu Gly Arg Cys Ile Ala Glu Gly Trp Thr Leu Glu Arg Val
                5                   10                  15

Ala Val Lys Gln Val Ser Trp Phe Leu Ile Tyr Ser Trp Val Cys Ser
                20                  25                  30

Gly Val Cys Arg Gly Val Ser Val Pro Glu Gln Gly Gly Gly Gly Gln
            35                  40                  45

Lys Ala Gly Ala Phe Thr Cys Leu Ser Asn Ser Ile Tyr Arg Ile Asp
    50                  55                  50

Cys His Trp Ser Ala Pro Glu Leu Gly Gln Glu Ser Arg Ala Trp Leu
65                  70                  75                  80

Leu Phe Thr Ser Asn Gln Val Thr Glu Ile Lys His Lys Cys Thr Phe
                85                  90                  95

Trp Asp Ser Met Cys Thr Leu Val Leu Pro Phe Glu Glu Val Phe Leu
            100                 105                 110

Pro Phe Asp Asn Phe Thr Ile Thr Leu His Arg Cys Ile Met Gly Gln
        115                 120                 125

Glu Gln Val Ser Leu Val Asp Ser Gln Tyr Leu Pro Arg Arg His Ile
130                 135                 140

Lys Leu Asp Pro Pro Ser Asp Leu Gln Ser Asn Val Ser Ser Gly Arg
145                 150                 155                 160

Cys Val Leu Thr Trp Gly Ile Asn Leu Ala Leu Glu Pro Leu Ile Thr
                165                 170                 175

Ser Leu Ser Tyr Glu Leu Ala Phe Lys Arg Gln Glu Glu Ala Trp Glu
            180                 185                 190

Ala Arg His Lys Lys Asp Arg Ile Val Gly Val Thr Trp Leu Ile Leu
        195                 200                 205
```

```
Glu Ala Val Glu Leu Asn Pro Glu Lys Arg Met
    210                 215
```

(2) INFORMATION FOR SEQ ID NO: 10:

(i) SEQUENCE CHARACTERISTICS:
        (A) LENGTH: 522 amino acid residues
        (B) TYPE: amino acid
        (D) TOPOLOGY: linear (xi) SEQUENCE DESCRIPTION: SEQ ID NO: 10:

```
Met Gly Leu Gly Arg Cys Ile Trp Glu Gly Trp Thr Leu Glu Ser Glu
              5                  10                  15
Ala Leu Arg Arg Asp Met Gly Thr Trp Leu Ala Cys Ile Cys Ile
             20                  25                  30
Cys Thr Cys Val Cys Leu Gly Val Ser Val Thr Gly Glu Gly Gln Gly
         35                  40                  45
Pro Arg Ser Arg Thr Phe Thr Cys Leu Thr Asn Asn Ile Leu Arg Ile
     50                  55                  60
Asp Cys His Trp Ser Ala Pro Glu Leu Gly Gln Gly Ser Ser Pro Trp
 65                  70                  75                  80
Leu Leu Phe Thr Ser Asn Gln Ala Pro Gly Gly Thr His Lys Cys Ile
                 85                  90                  95
Leu Arg Gly Ser Glu Cys Thr Val Val Leu Pro Pro Glu Ala Val Leu
            100                 105                 110
Val Pro Ser Asp Asn Phe Thr Ile Thr Phe His His Cys Met Ser Gly
            115                 120                 125
Arg Glu Gln Val Ser Leu Val Asp Pro Glu Tyr Leu Pro Arg Arg His
130                 135                 140
Val Lys Leu Asp Pro Pro Ser Asp Leu Gln Ser Asn Ile Ser Ser Gly
145                 150                 155                 160
His Cys Ile Leu Thr Trp Ser Ile Ser Pro Ala Leu Glu Pro Met Thr
                165                 170                 175
Thr Leu Leu Ser Tyr Glu Leu Ala Phe Lys Lys Gln Glu Glu Ala Trp
            180                 185                 190
Glu Gln Ala Gln His Arg Asp His Ile Val Gly Val Thr Trp Leu Ile
        195                 200                 205
Leu Glu Ala Phe Glu Val Asp Pro Gly Phe Ile His Glu Ala Arg Leu
    210                 215                 220
Arg Val Gln Met Ala Thr Leu Glu Asp Asp Val Val Glu Glu Glu Arg
225                 230                 235                 240
Tyr Thr Gly Gln Trp Ser Glu Trp Ser Gln Pro Val Cys Phe Gln Ala
                245                 250                 255
Pro Gln Arg Gln Gly Pro Leu Ile Pro Pro Trp Gly Trp Pro Gly Asn
            260                 265                 270
Thr Leu Val Ala Val Ser Ile Phe Leu Leu Leu Thr Gly Pro Thr Tyr
        275                 280                 285
Leu Leu Phe Lys Leu Ser Pro Arg Val Lys Arg Ile Phe Tyr Gln Asn
    290                 295                 300
Val Pro Ser Pro Ala Met Phe Phe Gln Pro Leu Tyr Ser Val His Asn
305                 310                 315                 320
Gly Asn Phe Gln Thr Trp Met Gly Ala His Arg Ala Gly Val Leu Leu
                325                 330                 335
Ser Gln Asp Cys Ala Gly Thr Pro Gln Gly Ala Leu Glu Pro Cys Val
            340                 345                 350
```

```
Gln Glu Ala Thr Ala Leu Leu Thr Cys Gly Pro Ala Arg Pro Trp Lys
            355                 360                 365

Ser Val Ala Leu Glu Glu Gln Glu Gly Pro Gly Thr Arg Leu Pro
    370                 375                 380

Gly Asn Leu Ser Ser Glu Asp Val Leu Pro Ala Gly Cys Thr Glu Trp
385                 390                 395                 400

Arg Val Gln Thr Leu Ala Tyr Leu Pro Gln Glu Asp Trp Ala Pro Thr
                405                 410                 415

Ser Leu Thr Arg Pro Ala Pro Pro Asp Ser Glu Gly Ser Arg Ser Ser
            420                 425                 430

Ser Ser Ser Ser Ser Ser Asn Asn Asn Tyr Cys Ala Leu Gly
        435                 440                 445

Cys Tyr Gly Gly Trp His Leu Ser Ala Leu Pro Gly Asn Thr Gln Ser
    450                 455                 460

Ser Gly Pro Ile Pro Ala Leu Ala Cys Gly Leu Ser Cys Asp His Gln
465                 470                 475                 480

Gly Leu Glu Thr Gln Gln Gly Val Ala Trp Val Leu Ala Gly His Cys
                485                 490                 495

Gln Arg Pro Gly Leu His Glu Asp Leu Gln Gly Met Leu Leu Pro Ser
            500                 505                 510

Val Leu Ser Lys Ala Arg Ser Trp Thr Phe
            515                 520

(2) INFORMATION FOR SEQ ID NO: 11:

(i) SEQUENCE CHARACTERISTICS:
        (A) LENGTH: 307 amino acid residues
        (B) TYPE: amino acid
        (D) TOPOLOGY: linear (xi) SEQUENCE DESCRIPTION: SEQ ID NO: 11:

Met Gly Leu Gly Arg Cys Ile Trp Glu Gly Trp Thr Leu Glu Ser Glu
                5                  10                  15

Ala Leu Arg Arg Asp Met Gly Thr Trp Leu Leu Ala Cys Ile Cys Ile
                20                  25                  30

Cys Thr Cys Val Cys Leu Gly Val Ser Val Thr Gly Glu Gly Gln Gly
            35                  40                  45

Pro Arg Ser Arg Thr Phe Thr Cys Leu Thr Asn Asn Ile Leu Arg Ile
50                  55                  60

Asp Cys His Trp Ser Ala Pro Glu Leu Gly Gln Gly Ser Ser Pro Trp
65                  70                  75                  80

Leu Leu Phe Thr Ser Asn Gln Ala Pro Gly Gly Thr His Lys Cys Ile
                85                  90                  95

Leu Arg Gly Ser Glu Cys Thr Val Val Leu Pro Pro Glu Ala Val Leu
            100                 105                 110

Val Pro Ser Asp Asn Phe Thr Ile Thr Phe His His Cys Met Ser Gly
            115                 120                 125

Arg Glu Gln Val Ser Leu Val Asp Pro Glu Tyr Leu Pro Arg Arg His
        130                 135                 140

Val Lys Leu Asp Pro Pro Ser Asp Leu Gln Ser Asn Ile Ser Ser Gly
145                 150                 155                 160

His Cys Ile Leu Thr Trp Ser Ile Ser Pro Ala Leu Glu Pro Met Thr
                165                 170                 175

Thr Leu Leu Ser Tyr Glu Leu Ala Phe Lys Lys Gln Glu Glu Ala Trp
            180                 185                 190
```

```
Glu Gln Ala Gln His Arg Asp His Ile Val Gly Val Thr Trp Leu Ile
            195                 200                 205

Leu Glu Ala Phe Glu Val Asp Pro Gly Phe Ile His Glu Ala Arg Leu
        210                 215                 220

Arg Val Gln Met Ala Thr Leu Glu Asp Asp Val Glu Glu Glu Arg
225                 230                 235                 240

Tyr Thr Gly Gln Trp Ser Glu Trp Ser Gln Pro Val Cys Phe Gln Ala
                245                 250                 255

Pro Gln Arg Gln Gly Pro Leu Ile Pro Pro Trp Gly Trp Pro Gly Asn
            260                 265                 270

Thr Leu Val Ala Val Ser Ile Phe Leu Leu Leu Thr Gly Pro Thr Tyr
        275                 280                 285

Leu Leu Phe Lys Leu Ser Pro Arg Leu Gly Trp Gly Pro Thr Gly Pro
    290                 295                 300

Val Cys Cys
305

(2) INFORMATION FOR SEQ ID NO: 12:

(i) SEQUENCE CHARACTERISTICS:
        (A) LENGTH: 536 amino acid residues
        (B) TYPE: amino acid
        (D) TOPOLOGY: linear (xi) SEQUENCE DESCRIPTION: SEQ ID NO: 12:

Met Leu Trp Leu Val Val Pro Gly Cys Thr Leu His Ser Arg Lys Gly
                5                   10                  15

Ala Leu Ser Gln Ser Leu Ala Gly Trp Thr Leu Glu Ser Glu Ala Leu
            20                  25                  30

Arg Arg Asp Met Gly Thr Trp Leu Leu Ala Cys Ile Cys Ile Cys Thr
        35                  40                  45

Cys Val Cys Leu Gly Val Ser Val Thr Gly Glu Gly Gln Gly Pro Arg
    50                  55                  60

Ser Arg Thr Phe Thr Cys Leu Thr Asn Asn Ile Leu Arg Ile Asp Cys
65                  70                  75                  80

His Trp Ser Ala Pro Glu Leu Gly Gln Gly Ser Ser Pro Trp Leu Leu
                85                  90                  95

Phe Thr Ser Asn Gln Ala Pro Gly Gly Thr His Lys Cys Ile Leu Arg
            100                 105                 110

Gly Ser Glu Cys Thr Val Val Leu Pro Pro Glu Ala Val Leu Val Pro
        115                 120                 125

Ser Asp Asn Phe Thr Ile Thr Phe His His Cys Met Ser Gly Arg Glu
    130                 135                 140

Gln Val Ser Leu Val Asp Pro Glu Tyr Leu Pro Arg Arg His Val Lys
145                 150                 155                 160

Leu Asp Pro Pro Ser Asp Leu Gln Ser Asn Ile Ser Ser Gly His Cys
                165                 170                 175

Ile Leu Thr Trp Ser Ile Ser Pro Ala Leu Glu Pro Met Thr Thr Leu
            180                 185                 190

Leu Ser Tyr Glu Leu Ala Phe Lys Lys Gln Glu Glu Ala Trp Glu Gln
        195                 200                 205

Ala Gln His Arg Asp His Ile Val Glu Val Thr Trp Leu Ile Leu Glu
    210                 215                 220

Ala Phe Glu Leu Gln Pro Gly Phe Ile His Glu Ala Arg Leu Arg Val
225                 230                 235                 240
```

```
Gln Met Ala Thr Leu Gly Asp Asp Val Val Glu Glu Glu Arg Tyr Thr
            245             250                     255

Gly Gln Trp Ser Glu Trp Ser Gln Pro Val Cys Phe Gln Arg Pro Gln
            260             265                     270

Arg Gln Gly Pro Leu Ile Pro Pro Trp Gly Trp Pro Gly Asn Thr Leu
        275                 280                 285

Val Ala Val Ser Ile Phe Leu Leu Leu Thr Gly Pro Thr Tyr Leu Leu
    290                 295                 300

Phe Lys Leu Ser Pro Arg Val Lys Arg Ile Phe Tyr Gln Asn Val Pro
305                 310                 315                 320

Ser Pro Ala Met Phe Phe Gln Pro Leu Tyr Ser Val His Asn Gly Asn
            325                 330                 335

Phe Gln Thr Trp Met Gly Ala His Arg Ala Gly Val Leu Leu Ser Gln
            340                 345                 350

Asp Cys Ala Gly Thr Pro Gln Gly Ala Leu Gly Pro Cys Val Gln Glu
            355                 360                 365

Ala Thr Ala Leu Leu Thr Cys Gly Pro Ala Arg Pro Trp Lys Ser Val
        370                 375                 380

Ala Leu Gly Glu Glu Gln Glu Gly Pro Gly Thr Arg Leu Pro Gly Asn
385                 390                 395                 400

Leu Ser Ser Glu Asp Val Leu Pro Ala Gly Cys Thr Glu Trp Arg Val
                405                 410                 415

Gln Thr Leu Ala Tyr Leu Pro Gln Glu Asp Trp Ala Pro Thr Ser Leu
            420                 425                 430

Thr Arg Pro Ala Pro Pro Asp Ser Glu Gly Ser Arg Ser Ser Ser Ser
        435                 440                 445

Ser Ser Ser Ser Ser Asn Asn Asn Asn Tyr Cys Ala Leu Gly Cys Tyr
    450                 455                 460

Gly Gly Trp His Leu Ser Ala Leu Pro Gly Asn Thr Gln Ser Ser Gly
465             470                 475                 480

Pro Ile Pro Ala Leu Ala Cys Gly Leu Ser Cys Asp His Gln Gly Leu
            485                 490                 495

Glu Thr Gln Gln Gly Val Ala Trp Val Leu Ala Gly His Cys Gln Arg
            500                 505                 510

Pro Gly Leu His Glu Asp Leu Gln Gly Met Leu Leu Pro Ser Val Leu
        515                 520                 525

Ser Lys Ala Arg Ser Trp Thr Phe
530                 535
```